(12) United States Patent  (10) Patent No.: US 8,563,459 B2
Larson et al.  (45) Date of Patent: Oct. 22, 2013

(54) FIXED-BED HYDROSILYLATION CATALYST COMPLEXES AND RELATED METHODS

(75) Inventors: Gerald L. Larson, Newtown, PA (US); Barry C. Arkles, Dresher, PA (US); Rudolph A. Cameron, Bensalem, PA (US)

(73) Assignee: Gelest Technology, Inc., Morrisville, PA (US)

( * ) Notice: Subject to any disclaimer, the term of this patent is extended or adjusted under 35 U.S.C. 154(b) by 295 days.

(21) Appl. No.: 12/770,895

(22) Filed: Apr. 30, 2010

(65) Prior Publication Data

US 2010/0280266 A1   Nov. 4, 2010

Related U.S. Application Data

(60) Provisional application No. 61/174,914, filed on May 1, 2009.

(51) Int. Cl.
C07F 7/08 (2006.01)
B01J 31/12 (2006.01)
B01J 8/02 (2006.01)

(52) U.S. Cl.
USPC ........... 502/155; 502/154; 422/211; 556/453; 556/478; 548/300.1

(58) Field of Classification Search
USPC .................. 502/154; 548/300.1; 446/453
See application file for complete search history.

(56) References Cited

U.S. PATENT DOCUMENTS 6,803,440 B2   10/2004   Marko et al.

FOREIGN PATENT DOCUMENTS

| DE | 30 42 410 C2 | 5/1982 |
| DE | 602 04 284 T2 | 2/2006 |
| DE | 10 2005 037 500 A1 | 2/2007 |
| WO | WO 2005/016941 A1 | 2/2005 |

OTHER PUBLICATIONS

Sasaki et al., Journal of Molecular Catalysis A: Chemical 279 (2008), p. 200-209.*
Review of Synthesis of Supported Palladium Catalysts, online publication on 2004.*
Aerosil fumed silica product catalogs (2012).*
Mesh value and particle size conversion (2012).*
Aerosil 300 particle size by EVONIK industries (2012).*

* cited by examiner

Primary Examiner — Yong Chu
(74) Attorney, Agent, or Firm — Flaster/Greenberg P.C.

(57) ABSTRACT

The invention includes a fixed-bed catalyst complex that includes (i) a metal carbene catalyst, wherein the metal is platinum, and (ii) a catalyst support that includes one or more of silica, alumina and/or glass. The invention provides a fixed-bed catalyst complex that includes a catalyst complex including a carbene chosen from those represented by at least one of Formulae (I), (II), (III), and (IV):

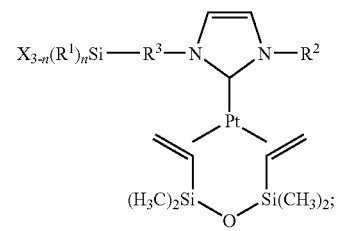

I

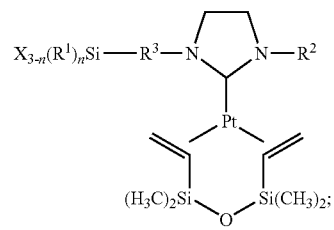

II

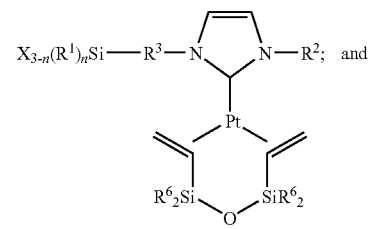

III

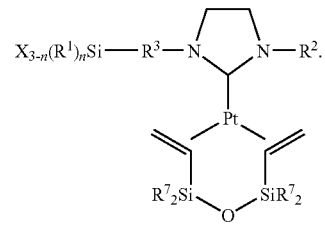

IV

Where the vales of X and $R^1$ to $R^7$ are specifically defined. The complex also includes a catalyst support that comprises silica, related reaction products, and related reaction systems.

14 Claims, No Drawings

FIXED-BED HYDROSILYLATION CATALYST COMPLEXES AND RELATED METHODS

CROSS REFERENCE TO RELATED APPLICATION

This application claims the benefit of priority under 35 U.S.C. §119(e) to U.S. patent application Ser. No. 61/174,914, filed May 1, 2009, the contents of which are incorporated herein by reference.

BACKGROUND OF THE INVENTION

Hydrosilylation reactions are a commercially significant industrial method for the formation of the silicon-carbon bond. This general methodology is employed in the formation of several commercial organosilanes, of a wide variety of organofunctional silicones and in the formation of cross-linked silicones. At commercial scale, the reaction is facilitated by a catalyst, usually a metal catalyst where the metal is of the platinum metal group metals.

Use of these types of catalysts is indisputably advantageous but does carry drawbacks. For example, the costs contributed to the manufacturing process by the use of new amounts of catalyst for each reaction cycle are relatively great, as are the costs associated with disposal of reaction waste containing the unrecyclable catalyst. Moreover, residues of the catalyst material may remain in or become incorporated into the final product, imparting an undesirable color.

Thus, there remains a need in the art for a catalyst complex and associated methods that address these disadvantages.

BRIEF SUMMARY OF THE INVENTION

The invention includes a stable fixed-bed catalyst complex that includes (i) a metal carbene catalyst, wherein the metal is platinum, and (ii) a catalyst support that includes one or more of silica, alumina and/or glass.

The invention provides a fixed-bed catalyst complex that includes a catalyst including a carbene chosen from those represented by at least one of Formulae (I), (II), (III), and (IV):

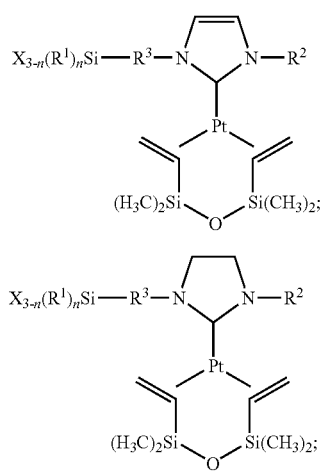

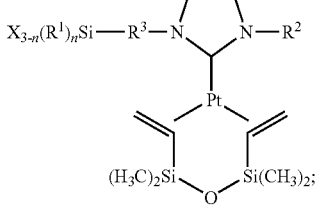

In any of the Formulae I-IV, n is independently an integer of 1 to 3, or alternatively, an integer of 0 to 2. The "X" may be independently chosen from a chlorine atom; the group $OR^4$, wherein $R^4$ is independently chosen from a hydrocarbyl group of 1 to 8 carbon atoms; and the group $NR^5{}_2$, wherein $R^5$ is independently chosen from a hydrocarbyl group of 1 to 8 carbon atoms.

$R^1$ and $R^3$ are each independently chosen from a hydrocarbyl group having 1 to 8 carbon atoms. $R^2$ is independently chosen from a hydrocarbyl group having 1 to 8 carbon atoms and $R^3$—$Si(R^1)_nX_{3-n}$, wherein X is independently chosen from: a chlorine atom; the group $OR^4$, and the group $NR^5{}_2$, wherein each of $R^1$, $R^4$, and $R^5$ is independently chosen from a hydrocarbyl group of 1 to 8 carbon atoms.

$R^6$ and $R^7$ are independently chosen from a hydrocarbyl group having 1 to 12 carbon atoms. The complex also includes a catalyst support that comprises silica.

Also encompassed within the scope of the invention are methods of preparing a recyclable hydrosilylation catalyst complex. Such methods include forming a fixed-bed catalyst complex by affixing a carbene catalyst chosen from those represented by Formulae (I), (II), (III), and (IV) (as defined above) and a catalyst support. The support may comprise silica. The recyclable hydrosilylation catalyst complex formed is capable of facilitating at least 3 cycles of hydrosilylation reaction with substantially minimal degradation of reaction efficiency.

The invention further includes cyclic processes for forming a bond between a carbon atom of a first molecule and a silicon atom of a second molecule by hydrosilylation. Such methods include providing a quantity of the first molecule and a quantity of the second molecule; reacting the first molecule with the second molecule in the presence of an effective amount of a catalyst complex to form a reaction product that contains a carbon-silicon bond formed by hydrosilylation; removing the reaction product; and repeating the prior steps with no addition of new catalyst or catalyst complex. The catalyst complex used may include a catalyst comprising a carbene chosen from those represented by Formulae (I), (II), (III), and IV) (as defined above), and a catalyst support that includes silica.

Also included with the scope of the invention are supported catalyst continuous reactor systems, methods of preparing the catalyst complex of the invention, and related reaction products, such as those that contain residual platinum in an amount no greater than about 0.01 ppm to about 20 ppm.

DETAILED DESCRIPTION OF THE INVENTION

Provided by the invention are fixed-bed catalyst complexes that may be used in a process employing a fixed-bed reactor to catalyze hydrosilylation reactions and form carbon-silicon bonds. The fixed-bed catalyst complexes can be recycled or re-used to catalyze at least two additional reaction cycles. Also included within the scope of the invention are methods for preparing such catalyst complexes and cyclic processes for forming a bond between a carbon atom of a first molecule and a silicon atom of a second molecule by hydrosilylation.

The fixed-bed catalyst complexes include at least a catalyst and a catalyst support. Platinum may be preferred.

In an embodiment, the carbene catalyst is a platinum carbene. Such carbenes may include any that have the structure represented by any one of Formulae (I), (II), (III) and/or (IV):

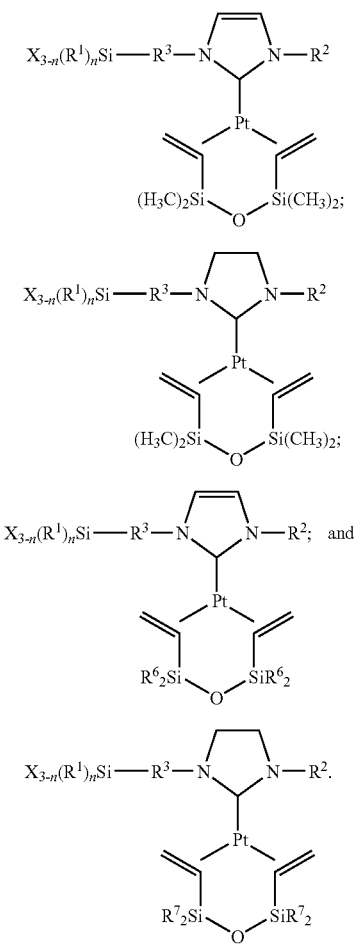

In each of the Formulae I-IV n is independently an integer of 1 to 3, or alternatively, an integer of 0 to 2.

In each of Formulae I to IV, X may be independently a chlorine or other halogen atom; the group $OR^4$, where $R^4$ is independently a hydrocarbyl group of 1 to 8 carbon atoms, alternatively, of 1 or 2 carbon atoms; and the group $NR^5{}_2$, where $R^5$ may be independently a hydrocarbyl group of 1 to 8 carbon atoms, an aryl group, a phenyl group, and/or any hydrocarbyl group of 1 to 2 carbon atoms.

In an embodiment, the $R^1$ and $R^3$ groups of Formulae I to IV may independently represent a hydrocarbyl group having 1 to 8 carbon atoms. Alternatively, the group represented by $R^1$ may independently contain 1 to 5 carbon atoms, and/or be a methyl or ethyl group, and the group represented by $R^3$ may contain 1 to 3 carbon atoms.

In various embodiments of the invention, $R^2$ may be chosen from a hydrocarbyl group having 1 to 8 carbon atoms, preferably 1 or 2 carbons atoms or be a phenyl group or an aryl group. In an embodiment, one or all of the groups represented by $R^2$ is $R^3$—$Si(R^1)_nX_{3-n}$, and X; $R^1$ and $R^3$ are the same as defined above. Examples of suitable groups may include, but are not limited to, a methyl group; an ethyl group; n-propyl; n-butyl; isopropyl; cyclohexyl; tent-butyl; neohexyl; phenyl; 2,4-dimethylphenyl; 2,4,6-trimethylphenyl; and 2,6-diisopropylphenyl.

In any of Formulae I to IV, $R^6$ may be independently chosen from a hydrocarbyl group having 1 to 12 carbon atoms, preferably 1 to 2 carbon atoms, an aryl group or a phenyl group. $R^7$ may be independently a hydrocarbyl group having 1 to 12 carbon atoms, preferably 1 to 2 carbon atoms, or an aryl or a phenyl group. Suitable specific examples may include those listed above for $R^2$.

Any one or more of the hydrocarbyl groups described above as within the definition of Formulae I to IV may be branched or linear and a specific molecule may contain all branched groups, all linear groups or a combination of both. In addition the carbons of these groups (as well as those present in the skeleton structures themselves), may be substituted or unsubstituted.

The catalyst may include more than one catalyst; for example, it may include additional catalysts of any type, including other metal carbene catalysts.

The complex also includes a catalyst support. Such support may be silica, alumina or glass. If silica, it may be preferred that the silica is a precipitated silica. In some embodiments that silica may have a BET surface area of about 300 to about 800 m²/g. It may be desirable that the silica chosen for use as the catalyst support has a mesh value of about 35 to about 500 or about 60 to about 400.

To prepare the catalyst complex of the invention, any method in the art may be used. An example for preparing the recyclable or reusable catalyst complex on the invention includes contacting the catalyst(s) in any form described above with the catalyst support(s) as described above. The catalyst complex that is formed is capable of catalyzing at least three hydrosilylation reaction cycles with substantially minimal degradation of reaction efficiency. Alternatively, the catalyst complex that is formed is capable of catalyzing at least five to at least one hundred or more hydrosilylation reaction cycles without addition of any new catalyst.

Also included in the invention are methods of preparing recyclable hydrosilylation catalyst complexes. Such methods include forming a fixed-bed catalyst complex. The fixed-bed catalyst is formed by combining any of the carbene catalysts described above and a catalyst support that includes silica.

In an embodiment, the catalyst complex is capable of catalyzing at least two cycles of hydrosilylation reaction with substantially minimal degradation of reaction efficiency. In some embodiments the catalyst complex is capable of catalyzing at least five, at least ten, at least fifteen, at least twenty, and/or at least twenty-five cycles of hydrosilylation reaction with substantially minimal degradation of reaction efficiency. By "substantially minimal degradation of reaction efficiency" it is meant that a single reaction cycle results in the conversion of about 80% to about 100%, about 90% to about 99% or about 95% to about 97% of a first reactant to a final product by hydrosilylation.

The catalyst complex is recyclable or reusable meaning that one may catalyze several reaction cycles as noted above in a time sequential manner, e.g., on the same day. Alternatively, one may catalyze several reaction cycles, as noted above, recover and store the catalyst complex for a time period, then re-initiate several additional reaction cycles using the same catalyst complex. For example, after recovery, one may store the catalyst complex for a time period ranging from about 1 to about 52 weeks, or about 100 weeks, or about 200 weeks or more, and subsequently carry out several additional reaction cycles with the recovered and stored catalyst complex. The reaction efficiency of these additional reactions may be substantially identical to or minimally less than that of the initial reaction cycle(s), that is the reaction runs while exhibiting substantially minimal degradation of reaction efficiency.

When storing the catalyst complex, it may be desirable to store the complex in an inert atmosphere, for example, under nitrogen.

Cyclic process for forming a bond between a carbon atom of a first molecule and a silicon atom of a second molecule are also provided. The first molecule and the second molecule may be any known or developed, including discrete compounds or polymers, or, in some cases, the individual monomers (or other repeating units, e.g., trimers, tetramers) of which the polymer is composed, as long as such molecule has at least one carbon atom and at least one silicon atom respectively. In some embodiments, the first molecule and the second molecule may be structurally identical. Suitable examples for the first molecule or the second molecule include olefins, silicones, and alkynes.

These processes include providing first quantity of the first molecule and a second quantity of the second molecule and reacting the first molecule and the second molecule in the presence of an effective amount of the catalyst complex(s) as described above. A reaction product is formed that contains at least one carbon-silicon bond formed by hydrosilylation. In an embodiment of the cyclic process, the reaction product is removed and the steps of providing reactants and reacting them in the presence of the catalyst complex are repeated. No new catalyst complex is added, however. The steps may be repeated numerous times without the addition of any new catalyst complex. For example, the steps may be repeated three times to one hundred times or more, without adding any new catalyst complex.

In some embodiments, these process may be carried out in a non-inert atmosphere, that is, for example, in the open air, or in an area containing non-inert gases.

EXAMPLES

Example 1

Preparation of an Exemplary Catalyst Precursor (N-Methyl-N'-(3-trimethoxysilylpropyl)imidazolium Iodide)

N-Methylimidazole (156.8 g; 1.91 mol) and 3-iodopropyltrimethoxysilane (569.8 g; 1.96 mol) were charged to a 1 L, 3-necked flask to form a reaction mixture. The reaction mixture was heated to 114° C. for eight hours during which time the color of the mixture changed from pale yellow to green and then to black. The crude reaction product was washed twice with 80 mL of toluene (2×40 mL). The resulting black oily liquid of N-methyl-N'-(3-trimethoxysilylpropyl) imidazolium iodide was dissolved in 286 g of methylene chloride and maintained as a solution.

Example 2

Preparation of an Exemplary Catalyst (N-Methyl-N'-(3-Trimethoxysilylpropyl)imidazolecarbene divinyltetramethyldisiloxane platinum complex)

The catalyst precursor from Example 1 (65.3 g of a 71.4% solution; 0.125 mol) was charged to a 500 mL, 3-necked flask along with dichloromethane (101 g) and platinum 1,3-divinyltetramethyldisiloxane complex (123.3 g of a 10% solution in xylene; 0.0626 mol Pt).

The reaction mixture was thoroughly stirred for 20 minutes. Subsequently, potassium tert-butoxide (18.0 g; 0.164 mol) was slowly added.

The reaction mixture was stirred for 16 hours at room temperature after which time it was filtered through a zeta pad to provide a yellow filtrate and a tacky filter cake. The filtrate was concentrated at 80° C. and 5 Torr to provide an oily liquid containing some solid. The solid was dissolved in tetrahydrofuran and filtered to give a yellow solution, which was concentrated at reduced pressure to give a dark viscous oil that was a catalyst, N-Methyl-N'-(3-trimethoxysilylpropyl)imidazolecarbene divinyltetramethyldisiloxane platinum.

Example 3

Preparation of Carbene Divinyltetramethyldisiloxane Platinum Catalyst Complex

Precipitated silica of 200-400 mesh (28.2 g; 0.469 mol) was charged to a 500 mL, 3-necked flask followed by the addition of toluene (181.2 g) and the catalyst prepared in Example 2 (3 g). The reaction mixture was heated to 85° C. for 15 hours during which time it turned a transparent dark color. The resulting dark solution was filtered through a zeta pad, washed with toluene (2×50 mL) and tetrahydrofuran (1×50 mL) and dried at reduced pressure. This provided 28 g of a very fine ash-colored solid. Analysis showed a platinum content of 1.37 percent.

Example 4

Hydrosilylation of 1-Octene with 1,1,3,3-Tetramethyldisiloxane Hydrosilylation Reaction 1-Octene (119.2 g; 1.06 mol) and 8.8 g of the catalyst complex prepared in Example 3 were charged to a 500 mL, 3-necked flask equipped with magnetic stirring, thermocouple, condenser and nitrogen atmosphere. The contents of the flask were heated to about 110° C. and 1,1,3,3-tetramethyldisiloxane (65.1 g; 0.485 mol) was slowly added dropwise. A slight exotherm was noted and the feed rate was adjusted to maintain a reaction temperature of 100° C. to 120° C. FTIR analysis of the reaction mixture after 2 hours from the start of the feed showed the complete absence of the Si—H absorbance at 2100 cm$^{-1}$ indicating that the reaction was complete. The FTIR of the undistilled crude reaction product was identical to that of an authentic sample of 1,3-di-n-octyltetramethyldisiloxane. GC analysis showed the undistilled product to be a single isomer of high purity.

Example 5

Hydrosilylation of 1-Octene with 1,1,3,3-Tetramethyldisiloxane-Recycled Catalyst Hydrosilylation Reaction After allowing the reaction product from Example 4 to cool and settle, the liquid product phase was siphoned away. The flask was charged with 1-octene (119.2 g; 0.469 mol) and 1,1,3,3-tetramethyldisiloxane (65.1 g; 0.485 mol) and the reaction carried out as in Example 4. This reaction/product removal sequence was repeated four times without loss of catalytic activity and with full conversion of the hydrosilylation reaction in short reaction times. The results of four consecutive recycle reactions are shown in Table 1.

TABLE 1

Results of Multiple Hydrosilylations of 1,1,3,3-Tetramethyldisiloxane and 1-Octene

| Run | Wt. of catalyst | Time (hours) | Conversion |
|---|---|---|---|
| 1 | 9.1 g | 2.0 | 100 |
| 2 | No new catalyst | 2.5 | 100 |
| 3 | No new catalyst | 2.5 | 100 |
| 4 | No new catalyst | 2.5 | 100 |

Example 6

Preparation of α,ω-Bis(n-octyl)polydimethylsiloxane—Silicone Hydrosilylation Polydimethylsiloxane, hydride-terminated (150.3 g; 11 eq. hydride) and 4.4 g of the catalyst complex prepared in Example 3 were added to a 500 mL flask and heated to about 100° C. To this was added 1-octene (36.6 g; 0.33 mol). The reaction showed an exotherm and the addition was regulated to maintain the reaction temperature between 110° and 120° C. After four hours the reaction was cooled and 163 g of the resulting hydrosilylation product siphoned away. Analysis showed no residual Si—H.

Example 7

Repeated Reaction Cycles

The reaction flask from Example 6 containing the original catalyst complex and with the liquid product phase removed was subjected to a repeat of the sequence in Example 6, above, to give 175 g of liquid product with no apparent lack of catalyst activity. This reaction-product-removal-reaction sequence was then repeated seven times. The results are summarized in Table 2. The platinum content of the residual, fixed-bed, still-active catalyst after run number eight was found to be 0.353 percent.

TABLE 2

Results of Multiple Hydrosilylations of Polydimethylsiloxane, Hydride-Terminated and 1-Octene

| Run | Wt. of catalyst | Time (hours) | Conversion | Platinum Conc. In Product |
|---|---|---|---|---|
| 1 | 4.4 g | 2.5 | 100 | 5 ppm |
| 2 | No new catalyst | 1.6 | 100 | ND |
| 3 | No new catalyst | 1.5 | 100 | 7 ppm |
| 4 | No new catalyst | 1.5 | 100 | ND |
| 5 | No new catalyst | 1.0 | 100 | ND |
| 6 | No new catalyst | 0.8 | 100 | ND |
| 7 | No new catalyst | 0.75 | 100 | ND |
| 8 | No new catalyst | 0.5 | 100 | <1 ppm |

Example 8

Catalyzed Hydrosilylation of Octadecene with Methyldichlorosilane

Example of a Hydrosilylation of an Olefin with a Chlorosilane

A 250 mL flask equipped with additional funnel and reflux condenser was charged with 4.5 g (0.318 mmol platinum) of the catalyst complex prepared in Example 3 and 126.3 g (0.50 mol) of 1-octadecene. The reaction mixture was heated to 85° C. and a small portion of methyldichlorosilane added. The reaction initiated immediately and the remainder of 60.3 g (0.524 mol) of the methyldichlorosilane was added at a rate sufficient to maintain the temperature between 85° and 100° C. in the absence of external heating. After one hour the reaction was cooled to room temperature and the solid catalyst complex allowed to settle. The supernatant liquid was siphoned away. GC analysis showed the reaction to be 100 percent converted to n-octadecylmethyldichlorosilane free from isomeric octadecylmethyldichlorosilanes. The same reaction flask was again charged with 126 g (0.50 mol) of octadecene and reacted with methyldichlorosilane as above. This sequence was repeated nine times without loss of catalyst activity and reaction times of one hour. The results are summarized in Table 3.

TABLE 3

Results of Multiple Hydrosilylations of Methyldichlorosilane and 1-Octadecene

| Run | Wt of catalyst | Time (hours) | Conversion |
|---|---|---|---|
| 1 | 4.5 g | 1.0 | 100 |
| 2 | No new catalyst | 1.0 | 100 |
| 3 | No new catalyst | 1.0 | 100 |
| 4 | No new catalyst | 1.0 | 100 |
| 5 | No new catalyst | 1.0 | 100 |
| 6 | No new catalyst | 1.0 | 100 |
| 7 | No new catalyst | 1.0 | 100 |
| 8 | No new catalyst | 1.0 | 100 |
| 9 | No new catalyst | 1.0 | 100 |
| 10 | No new catalyst | 1.0 | 100 |

Example 9

Preparation of α,ω-n-octylpolydimethylsiloxane

Example of Hydrosilylation with Aged Catalyst in the Presence of Air

Catalyst complex prepared as described in Example 6 (9.6 g), was maintained for six months under nitrogen and subsequently exposed to the air for 10 days. It was then charged to a 500 mL flask; the flask was then further charged with 150 g (0.143 mol) of hydride-terminated polydimethylsiloxane and 37.7 g (0.336 mol) of 1-octene.

The reaction apparatus was open to the air. Upon slowly warming the reaction mixture a significant exotherm occurred at 90° C. leading to a top temperature of 115° C. FTIR analysis of the reaction mixture after 0.5 hour revealed the complete absence of the Si—H stretch indicating completion of the reaction.

Example 10

Preparation of 1,2-Bis(trichlorosilyl)ethane—Example of Regiospecific Hydrosilylation of a Vinylsilane A 250 mL flask was charged with 10 g of catalyst complex prepared as described in Example 3, 52 mL of toluene, and 71.7 g (0.44 mol) of vinyltrichlorosilane. The reaction mixture was heated to 45° C. and the dropwise addition of trichlorosilane (62.5 g, 0.46 mol) was initiated. The temperature of the reaction was increased to 85° C. and continued at that temperature with further dropwise addition of the trichlorosilane until all of the trichlorosilane had been added and no further reflux was noted—about 60 minutes. GC analysis indicated that the reaction was fully converted. No evidence was found for the presence of the bis-(1,1-trichlorosilyl)ethane isomer.

Example 11

Preparation of Glass Bead-Supported Platinum Catalyst Complex 428.0 g of acid washed, porous glass beads were charged to a 1000 mL, 4-neck flask, followed by 300 g toluene, and 103.3 g of a 22% solution of catalyst complex as prepared in Example 3 in THF (36.96 mmol Pt). The pot was slowly heated to an initial reflux at 85° C. and the temperature slowly increased to 101° C. The reaction mixture changed from light yellow and transparent to hazy and non-transparent. The reaction mixture was held at this temperature for a total of 18 hours then cooled and the liquid siphoned away. The beads were washed with toluene (2×230 mL) and then with 320 g hexane and vacuum dried. 465.5 g of treated, colorless beads were collected.

Example 12

Preparation of n-Octyl-Terminated Polydimethylsiloxane Using Glass Bead-Supported Platinum Catalyst Complex 40.3 g of 1-Octene (0.360 mol) was charged to a 500 mL 3-necked flask followed by 150.8 g hydride terminated polydimethylsiloxane (Gelest DMS-H11) (0.147 mol) and 19.5 g of the catalyst complex on glass beads from Example 11. The system was thoroughly mixed, heated to and held at 100° C. for five hours. FTIR of a sample of the pot showed the absence of any absorbance in the 2100 cm$^{-1}$ region indicating that the hydrosilylation was complete. The reaction mixture was cooled to ambient temperature, the mother liquor siphoned off and the flask recharged with similar weights of 1-octene and the hydride-terminated DMS-H11. The new reaction mixture was mixed thoroughly, heated to and held at 110° C. for 4 hours. FTIR analysis showed only trace absorbance in the 2100 cm$^{-1}$ region indicating complete reaction. The cycle was repeated two more times for a total of four reactions with a single, original catalyst charge. In all four reactions the final product was water white, showing none of the off-color hues typically seen with the homogenous catalyst reactions.

| Run | Wt of catalyst | Time (hours) | Conversion |
|---|---|---|---|
| 1 | 19.6 g | 16 | 100 |
| 2 | No new catalyst | 4 | 100 |
| 3 | No new catalyst | 4 | 100 |
| 4 | No new catalyst | 4 | 100 |

Example 13

Preparation of Supported Catalyst Continuous Reactor System—Fixed-Bed Catalyst Continuous Reactor The supported catalyst continuous reactor system consisted of two stainless steel columns 18" in length and 1" in diameter. The columns were loosely packed with 280 g of 0.5 mm diameter beads treated with the catalyst complex as described in Example 11. The first column was configured with a six-point thermocouple to measure the temperature profile over the first two-thirds of the length of the column. The two columns were connected by a ¼" OD stainless steel tubing.

Both columns and the connecting tube were wrapped in heating tape in order to maintain the temperature of the reaction. The columns were heated to between 100° C. and 110° C. in order to maintain a reasonable reaction rate. A pre-mix of olefin and organosilane was prepared in a flask and was introduced via a peristaltic pump through a coil immersed in a heating bath at a temperature of about 100° C. This serves as a pre-heater for the reaction mixture prior to entering into catalyst column one and finally into catalyst column two and returning to the reservoir flask. The progress of the reaction was monitored by GC and/or FTIR analysis of the reservoir contents as a function of time.

Example 14

Preparation of 3-Octylheptamethyltrisiloxane—Example of a Fixed-Bed Continuous Hydrosilylation The reservoir in the reactor train described in Example 13 was charged with 722.3 g (3.25 mol) bis(trimethylsiloxy)methylsilane and 371.2 g (3.31 mol) of 1-octene. This mixture was thoroughly blended and circulated through the apparatus at a rate of 12.5 g per minute and a temperature of 100° C. GC analysis of the pot as a function of reaction time was evaluated. The results are shown in Table 4:

TABLE 4

| Time point | Percent conversion |
|---|---|
| After 2 hours | 23 |
| After 5 hours | 53.7 |
| After 9 hours | 77.3 |
| After 12 hours | 82.5 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A fixed-bed catalyst complex comprising:
a catalyst comprising a carbene chosen from those represented by at least one of Formulae (I), (II), (III), and (IV):

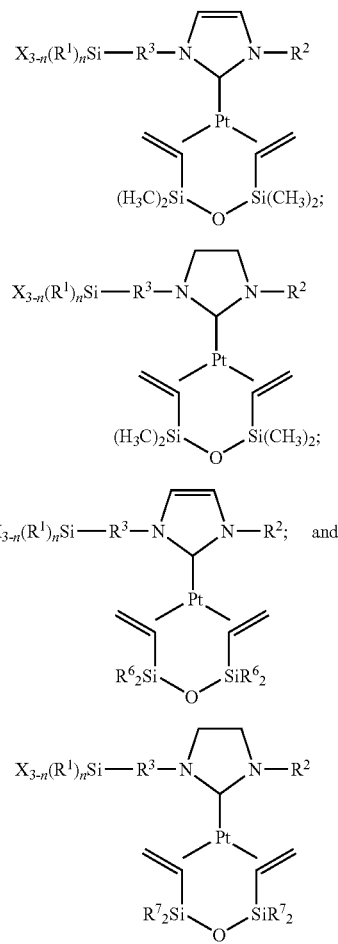

wherein, in any of the Formulae I-IV, n is independently an integer of 0 to 2, and: X is independently chosen from a chlorine atom; the group $OR^4$, wherein $R^4$ is independently chosen from a hydrocarbyl group of 1 to 8 carbon atoms; and the group $NR^5{}_2$, wherein $R^5$ is independently chosen from a hydrocarbyl group of 1 to 8 carbon atoms;

$R^1$ and $R^3$ are each independently chosen from a hydrocarbyl group having 1 to 8 carbon atoms; $R^2$ is independently chosen from a hydrocarbyl group having 1 to 8 carbon atoms and $R^3$—$Si(R^1)$—$X_{3-N}$, wherein X is independently chosen from: a chlorine atom; the group $OR^4$, and the group $NR^5{}_2$, wherein each of $R^1$, $R^4$, and $R^5$ is independently chosen from a hydrocarbyl group of 1 to 8 carbon atoms; $R^6$ and $R^7$, are independently chosen from a hydrocarbyl group having 1 to 12 carbon atoms; and a catalyst support that comprises silica.

2. The complex according to claim 1, wherein at least one of X is $OR^4$ and $R^4$ is independently chosen from a hydrocarbyl group of 1 to 2 carbon atoms.

3. The complex according to claim 1, wherein at least one of X is $NR^5{}_2$, and $R^5$ is independently chosen from an aryl group, a phenyl group, and a hydrocarbyl group of 1 to 2 carbon atoms.

4. The complex according to claim 1, wherein $R^1$ is independently chosen from a hydrocarbyl group of 1 to 5 carbon atoms.

5. The complex according to claim 1, wherein $R^3$ is independently chosen from a hydrocarbyl group of 1 to 3 carbon atoms.

6. The complex according to claim 1, wherein $R^2$ is independently chosen from an aryl group, a phenyl group and a hydrocarbyl group having 1 to 2 carbon atoms.

7. The complex according to claim 1, wherein $R^2$ is chosen from a methyl group; an ethyl group; n-propyl; n-butyl; isopropyl; cyclohexyl; tent-butyl; neohexyl; phenyl; 2,4-dimethylphenyl; 2,4,6-trimethylphenyl; and 2,6-diisopropylphenyl.

8. The complex according to claim 1, wherein $R^6$ is independently chosen from a hydrocarbyl group having 1 to 3 carbon atoms.

9. The complex according to claim 1, wherein $R^7$ is independently chosen from an aryl group, a phenyl group and a hydrocarbyl group having 1 to 3 carbon atoms.

10. The complex according to claim 1, wherein the catalyst support further includes an additional material chosen from alumina and glass.

11. The complex according to claim 1, wherein the silica is a precipitated silica.

12. The complex according to claim 1, wherein the silica has a BET surface area of about 300 to about 800 m$_2$g.

13. The complex according to claim 1, wherein the silica has a mesh value of about 100 to about 800.

14. The complex according to claim 1, wherein the silica has a mesh value of about 200 to about 400.

* * * * *